United States Patent [19]

Diamond et al.

[11] 3,969,401

[45] July 13, 1976

[54] α-AMINOPHENYLACETIC ACID COMPOUNDS AND DERIVATIVES

[75] Inventors: Julius Diamond, Lafayette Hill; Norman J. Santora, Roslyn, both of Pa.

[73] Assignee: William H. Rorer, Inc., Fort Washington, Pa.

[22] Filed: Aug. 14, 1973

[21] Appl. No.: 388,292

Related U.S. Application Data

[62] Division of Ser. No. 34,870, May 5, 1970, Pat. No. 3,864,384.

[52] U.S. Cl............................................. 260/518 A
[51] Int. Cl.²..................................... C07C 101/02
[58] Field of Search........................ 260/518 A, 519

[56] References Cited
UNITED STATES PATENTS 3,803,233  4/1974  Archer et al.................... 260/518 A

*Primary Examiner*—Anton H. Sutto
*Attorney, Agent, or Firm*—Erich M. H. Radde

[57] ABSTRACT

Certain substituted α-halo and α-mercaptophenylacetic acids and substituted phenylacetic acids having in α-position a sulfur-containing group, a cyano group, or an amino group, their substantially non-toxic esters, salts, and acid amides as well as 5-phenyl substituted 2-imino-4-oxothiazolidines and 5-phenyl substituted 2,4-dioxothiazolidines have a high anti-inflammatory, analgesic, and antipyretic activity, low toxicity, and/or a favorable therapeutic index with minor or no side-effects. Preferred compounds of this invention are α,m-dichloro-p-cyclohexylphenylacetic acids and its esters and salts.

6 Claims, No Drawings

α-AMINOPHENYLACETIC ACID COMPOUNDS AND DERIVATIVES

This application is a divisional application of copending application Ser. No. 34,870, filed May 5, 1970, now U.S. Pat. No. 3,864,384.

BACKGROUND OF THE INVENTION

1. Field of the Invention

The present invention relates to valuable novel substituted phenylacetic acids and more particularly to substituted α-halophenylacetic acids and substituted phenylacetic acids having in α-position a sulfur containing group, especially substituted α-mercaptophenylacetic acids, to a process of making such compounds, to pharmaceutical compositions containing the same, and to using such compositions in therapy as anti-inflammatory antipyretic, and analgesic agents.

2. Description of the Prior Art

A number of substituted phenylacetic acids and their esters have been tested for their anti-inflammatory, analgesic, antipyretic properties but none of them have been accepted by the medical profession for the treatment of humans or have been marketed by the pharmaceutical industry.

SUMMARY OF THE INVENTION

It is an object of the pesent invention to provide novel and valuable substituted phenylacetic acid compounds of high anti-inflammatory, analgesic, and antipyretic activity, low toxicity and/or a favorable therapeutic index with considerably reduced side-effects.

Another object of the present invention is to provide simple and effective processes of making such novel and substituted phenylacetic acid compounds.

Still another object of the present invention is to provide pharmaceutical compositions containing such novel and valuable substituted phenylacetic acid compounds.

A further object of the present invention is to provide a method of administering such pharmaceutical compositions for their anti-inflammatory, analgesic, and antipyretic activity.

Other objects and advantageous features of the present invention will become apparent as the description proceeds.

In principle the substituted phenylacetic acid compounds according to the present invention are compounds of the following Formula I

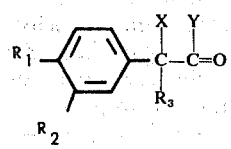

wherein $R_1$ is cycloalkyl with 5 to 7 carbon atoms in the cycloalkyl ring such as cyclohexyl, cyclopentyl, cycloheptyl; lower alkyl substituted cycloalkyl such as methyl cyclopentyl, methylcyclohexyl; straight-chain or branched alkyl with 1 to 8 carbon atoms; phenyl; or phenyl substituted by trifluoromethyl —$CF_3$, halogen, lower alkylsulfonyl —$SO_2R$, nitro, or cyano, such as trifluoromethylphenyl, chlorophenyl, methylsulfonylphenyl, nitrophenyl, cyanophenyl;

$R_2$ is halogen such as chloro, bromo, iodo, fluoro; nitro; cyano; trifluoromethyl —$CF_3$; lower alkylsulfonyl —$SO_2R$, such as methylsulfonyl; or hydrogen, if $R_1$ is substituted phenyl;

$R_3$ is hydrogen or lower alkyl with 1 to 8 carbon atoms such as methyl;

X is halogen such as chloro, bromo, iodo, fluoro; mercapto —SH; lower alkylmercapto —SR; lower alkylsulfonyl —$SO_2R$; thiocyano —SCN; cyano; sulfonate —$SO_3M$, wherein M is a substantially non-toxic alkali metal; thiosulfate —$S_2O_3M$; lower alkanoylthio —S.CO.R; lower alkylxanthyl

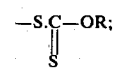

isothioureido

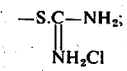

amino; lower alkylamino —NHR and di-(lower alkyl) amino

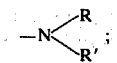

lower alkanoylamino —NH.CO.R; the group of the formula

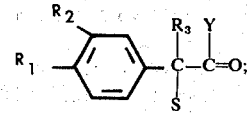

or the group of the formula

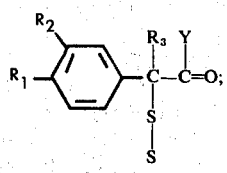

and

Y is hydroxyl; or the amido group

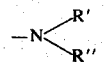

wherein R' and R'' are hydrogen, lower alkyl, aralkyl, such as benzyl, or R' and R'' together with the nitrogen atom to which they are attached, form a heterocyclic ring, such as the pyrrolidino, piperidino, piperazino, or the like heterocyclic ring; and wherein X and Y together with the two carbon atoms to which they are attached, form a heterocyclic ring of the formula

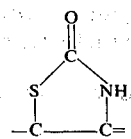

or a heterocyclic ring of the formula

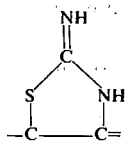

The present invention comprises also the substantially non-toxic, pharmaceutically acceptable esters and salts of the substituted phenylacetic acids of Formula I wherein Y is hydroxyl. Such esters are, for instance:

a. the esters with lower aliphatic alcohols such as with methanol, ethanol, n-propanol, isopropanol, n-butanol, isobutanol, n-amyl alcohol, isobutylcarbinol, n-hexanol, n-heptanol, n-octanol, monomethylether of ethylene glycol, allyl alcohol, diethylaminoethanol, piperidinoethanol, piperazinoethanol, pyrrolidinoethanol, and other alcohols with 1 to 8 carbon atoms;

b. the esters with alicyclic alcohols and alcohols of the terpene series, such as with cyclopentanol, cyclohexanol, 2-methylcyclohexanol, cyclohexylcarbinol, menthol, borneol, fenchyl alcohol, and other alicyclic alcohols with 6 to 14 carbon atoms;

c. the esters with hydroxyl substituted aryl compounds such as with phenol, cresol, guajacol, and other phenolic compounds with 6 to 14 carbon atoms;

d. the esters with aryl substituted alkanols such as benzyl alcohol, phenylethyl alcohol, anisalcohol, and other aryl substituted alkanols with 7 to 14 carbon atoms;

e. the esters with heterocyclic alcohols such as furfuralcohol and others.

The lower alkyl esters are the preferred esters.

Suitable substantially non-toxic, pharmaceutically acceptable salts of the substituted phenyl acetic acids of Formula I, wherein Y is hydroxyl, are, for instance, the alkali metal or alkaline earth metal salts, such as the sodium, potassium, or calcium salts, the ammonium salts, or the salts with organic bases such as the di-lower alkylammonium salts, for instance, the dimethylammonium salt, the diethylammonium salt, the hydroxy lower alkylammonium salts such as the β-hydroxyethylammonium salt, the piperazinium salt, the piperidinium salt, the lower alkyl benzyl-ammonium salts such as the α-methylbenzylammonium salt, and others.

The term "lower alkyl" as used herein and in the claims annexed hereto designates straight-chain or branched alkyl with 1 to 8 carbon atoms.

In particular the substituted phenylacetic acid compounds of the present invention are a. α-halophenylacetic acids of Formula II

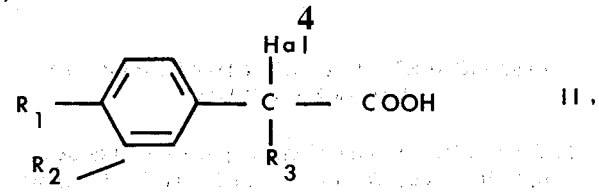

b. α-mercaptophenylacetic acids of Formula III,

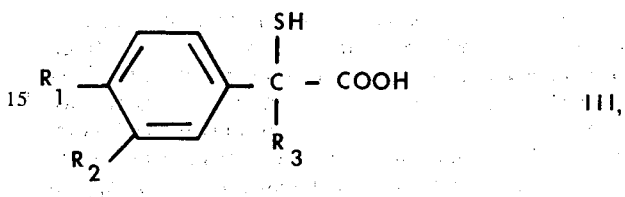

or c. α-sulfur derivatives of such α-mercaptophenylacetic acids of Formula IV

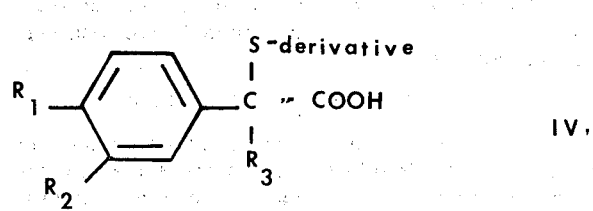

such as the corresponding sulfides, disulfides, thiosulfates, xanthates, isothiuronium halides, oxothiazolidines, and the like compounds which serve as latent forms or precursors of the α-mercaptophenylacetic acids of Formula II.

Not only the substituted phenylacetic acids of Formulas II to IV but also their non-toxic salts, the esters, and the amides of said substituted phenylacetic acids have proved to be useful anti-inflammatory, antipyretic, and analgesic agents and are used in reducing the inflammation and pain associated with polyarthritis in mammals.

The compounds of Formula I are administered preferably orally as their non-toxic salts or esters in the form of powder, granules, capsules, coated or uncoated compressed tablets, or as an aqueous suspension or solution. They may also be administered parenterally as a sterile aqueous solution of their non-toxic salts. Compounds that are especially useful include the α,m-diahalo-p-cycloalkylphenylacetic acids, α,o′-dihalo-p-biphenylylacetic acids, α,m-dihalo-p-lower alkylphenylacetic acids. The preferred compounds of this invention are α,m-dichloro-p-cyclohexylphenylacetic acid of Formula V

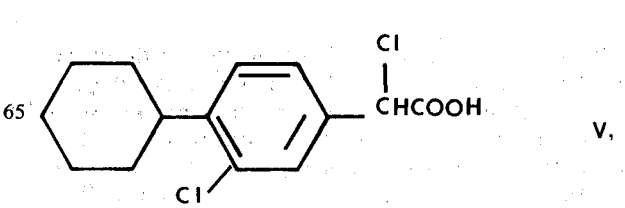

its lower alkyl esters, and its non-toxic salts; they are administered preferably orally in a dose range of 0.1 mg. to 10 mg. per kg. of body weight. The acute oral toxicity of the preferred compounds are relatively low.

The starting materials for producing the substituted α-halophenyl acetic acids according to Formula II are lower alkyl esters of the corresponding substituted phenylglycolic acid in which $R_1$ is lower alkyl ($C_1$ to $C_8$), cycloalkyl ($C_5$ to $C_7$), phenyl, halophenyl, nitrophenyl, trifluoromethylphenyl, cyanophenyl, or methylsulfonylphenyl; $R_3$ is hydrogen or lower alkyl; R is lower alkyl, and $R_2$ is halogen, nitro, cyano, trifluoromethyl, methylsulfonyl, or hydrogen (when $R_1$ is substituted phenyl). The substituted phenylglycolic acid lower alkyl esters of Formula VII are prepared by the method disclosed in copending patent application Ser. No. 767,058 now U.S. Pat. No. 3,704,313 from the lower alkyl esters of the corresponding substituted phenylglyoxylic acid of Formula VI either by catalytic hydrogenation when $R_3$ is hydrogen, or by reaction with a lower alkyl Grignard reagent when $R_3$ is lower alkyl, as illustrated by the following equation:

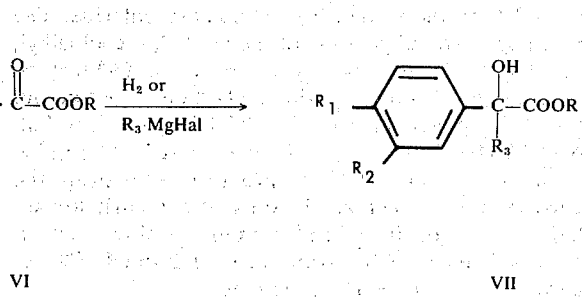

VI           VII

When $R_2$ is nitro, it is preferable to reduce the lower alkyl ester of Formula VIII of the substituted m-nitrophenylglycolic acid with sodium borohydride in methanol to obtain the corresponding lower alkyl ester of Formula IX of a substituted m-nitrophenylglycolic acid. This procedure is illustrated by the following equation:

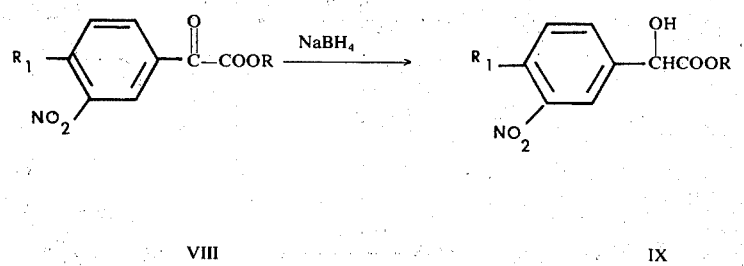

VIII           IX

Substituted m-fluorophenylglycolate esters of Formula XIII are also obtained by catalytic hydrogenation of the corresponding substituted m-nitrophenylglycolate esters of Formula X to give the substituted m-aminophenylglycolate esters of Formula XI which, after conversion to the diazonium fluoroborate of Formula XII are thermally decomposed to the substituted m-fluorophenylglycolate esters of Formula XIII as shown in the following equations:

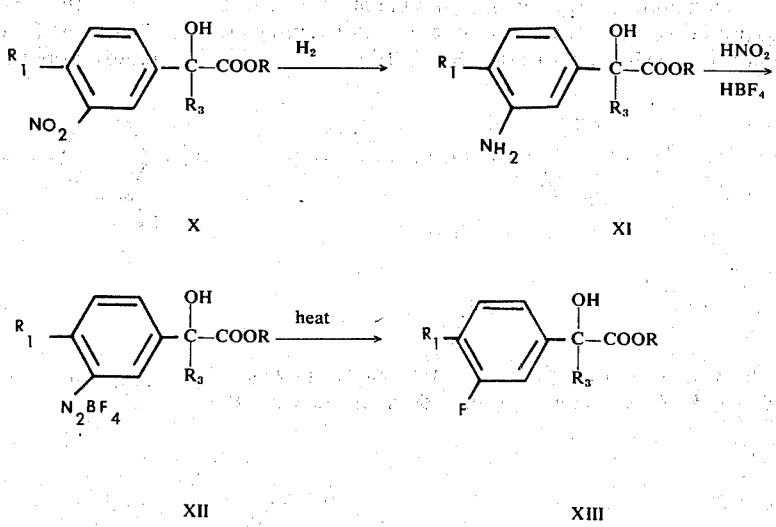

X           XI

XII           XIII

As stated above, the substituted phenylglyoxylic acid lower alkyl esters of Formula VI are produced according to the method of copending Pat. application Ser. No. 767,058 now U.S. Pat. No. 3,704,313 by reacting an alkylbenzene, a cycloalkylbenzene, or a biphenyl of Formula XIV with a lower alkyl oxalyl chloride of Formula XV in the presence of aluminum chloride. The resulting lower alkyl esters of the p-alkyl, p-cycloalkyl, of p-biphenylylglyoxylic acids of Formula XVI may be halogenated according to the method described in said U.S. Pat. application Ser. No. 767,058, now U.S. Pat. No. 3,704,313 or they may be nitrated with fuming nitric acid at about 0°C. to produce respectively the corresponding lower alkyl esters of a substituted m-halophenylglyoxylic acid of Formula XVII or a substituted m-nitrophenylglyoxylic acid of Formula IX according to the following equations:

alkyl ester of a substituted m-trifluoromethylphenylglyoxylic acid of Formula XIX by following the method described by Y. Kobayashi and I. Kumadaki in "Tetrahedron Letters" vol. 47, p. 4095 (1959).

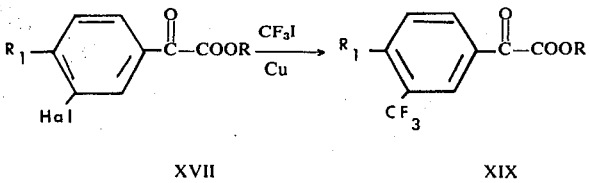

XVII          XIX

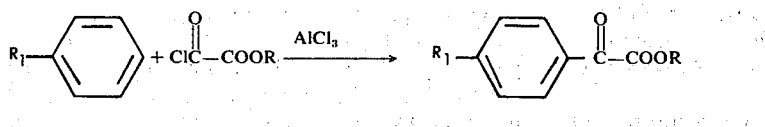

XIV    XV        XVI

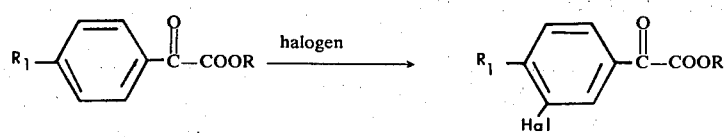

XVI        XVII

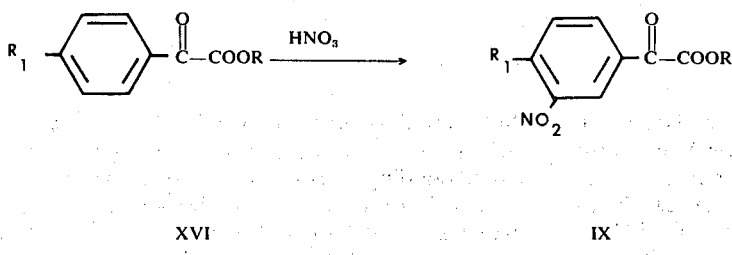

XVI        IX

Additional variations in $R_2$ are obtained by reacting a lower alkyl ester of a substituted m-halophenylglyoxylic acid of Formula XVII as follows:

a. with cuprous cyanide to quinoline at about 150°C. to produce a lower alkyl ester of a substituted m-cyanophenylglyoxylic acid of Formula XVIII:

c. with cuprous methanesulfinate in quinoline at about 150°C. to produce a lower alkyl ester of a substituted m-methylsulfonylphenylglyoxylic acid of Formula XX:

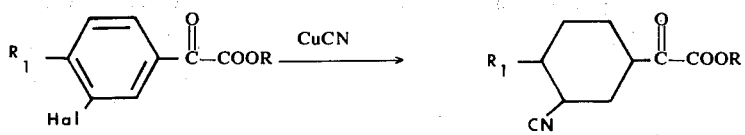

XVII        XVIII b. with trifluoromethyliodide and copper powder at about 150°C. in dimethylformamide to produce a lower

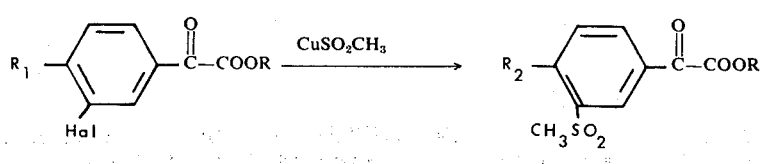

XVII        XX

The substituted phenylglycolic acid lower alkyl ester of Formula VII is reacted with a phosphorus trihalide, phosphorus pentahalide, phosphorus oxyhalide, sulfurylhalide, thionyl halide, or sulfur halide to produce a substituted α-halophenylacetic acid lower alkyl ester of Formula XXI in which Hal is F, Cl, Br, or I.

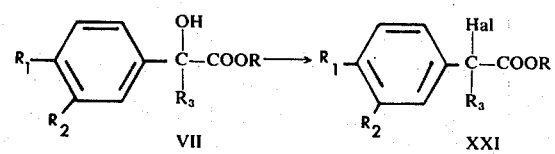

The ester of Formula XXI is heated with acetic acid containing the corresponding hydrogen halide to give a substituted α-halophenylacetic acid of Formula II.

The carboxylic acid of Formula II is reacted with an equivalent amount of a non-toxic alkali or alkaline earth bicarbonate, carbonate, or hydroxide to produce a substituted α-halophenylacetate salt of Formula XXII in which M is a non-toxic alkali metal or alkaline earth metal. Alternatively, the carboxylic acid may be reacted with an equivalent amount of a non-toxic amine, such as diethylamine, diethanolamine, piperazine, piperadine, α-methylbenzylamine, and others, to produce a substituted α-halophenylacetate salt of Formula XXII in which M is an ammonium group.

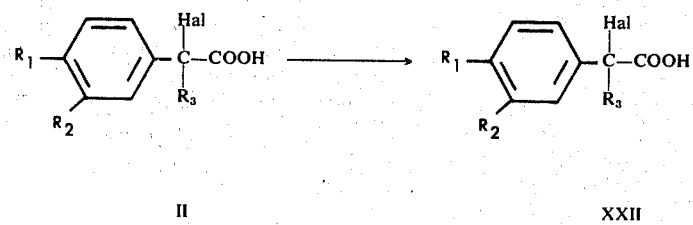

Reaction of the lower alkyl ester of a substituted α-halophenylacetic acid of Formula XXI with ammonia or a lower alkylamine leads to a substituted α-halophenylacetamide of Formula XXIII in which R is hydrogen or lower alkyl, and R' is hydrogen or lower alkyl.

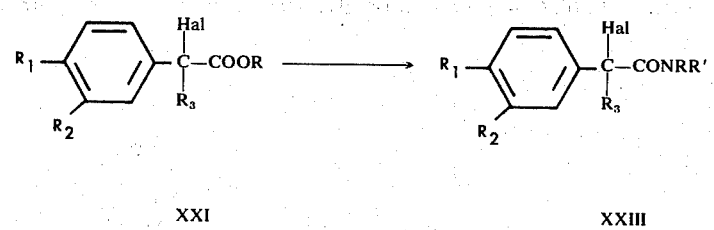

The substituted α-fluorophenylacetic acid derivatives of Formula XXV are also obtained from the corresponding α-iodo, α-bromo, or α-chlorophenylacetic acid derivatives of Formula XXIV by reaction with potassium fluoride at about 130°–200°C.

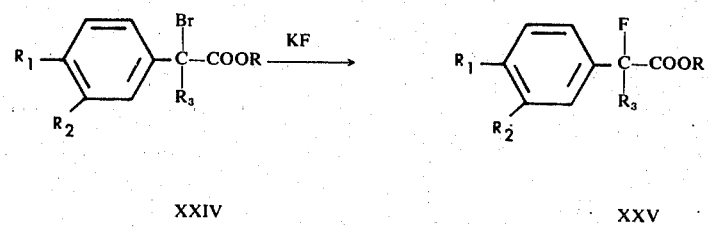

The substituted α-halophenylacetic acids of Formula II, their salts of Formula XXII, or amides of Formula XXIII, or their lower alkyl esters of Formula XXI may be reacted with various nucleophillic reagents to re-

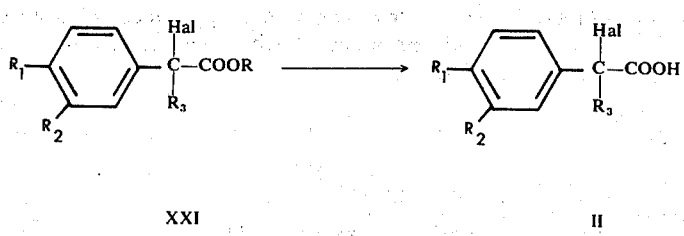

place the α-halogen group. In particular sulfur-containing nucleophilic reagents are used such as alkali hydrosulfides MSH, alkali sulfides $M_2S$, alkali thiolalkanoates MSCOR, alkali thiocyanates MSCN, alkali sulfites $M_2SO_3$, alkali thiosulfates $M_2SSO_3$, alkali alkanesulfinates $M_2SO_2R$, alkali alkylmercaptides MSR. With excess alkali hydrosulfide a mixture of a substituted α-mercaptophenylacetic acid derivative of Formula XXVI and the corresponding substituted α,α'-dithiodiacetic acid derivative of Formula XXVII are produced. The mercaptan and the disulfide may be separated by fractional crystallization of their salts. Reduction of the disulfide with zinc amalgam and dilute sulfuric acid produces the mercaptan. Oxidation of the mercaptan with dilute iodine solution gives the disulfide.

Hydrolysis of the imino compound of Formula XXVIII with hydrobromic acid in glacial acetic acid leads to a 5-substituted-2,4-dioxothiazolidine of Formula XXIX:

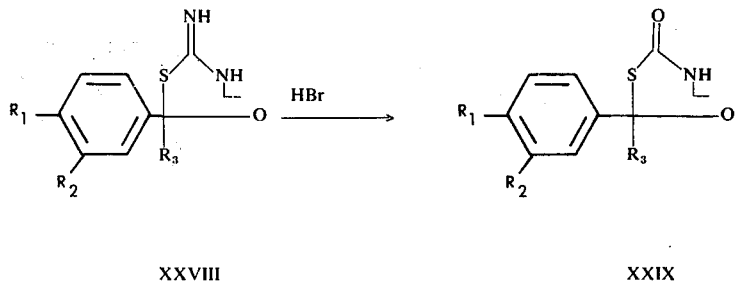

XXVIII     XXIX

Hydrolysis of the imino compound of the Formula XXVIII or the dioxothiazolidine of Formula XXIX with alkali hydroxide or alkali carbonate leads to a mixture of a substituted α-mercaptophenylacetic acid of Formula XXVI and a substituted α,α'-dithiodiacetic acid of Formula XXVII which may be separated by frac-

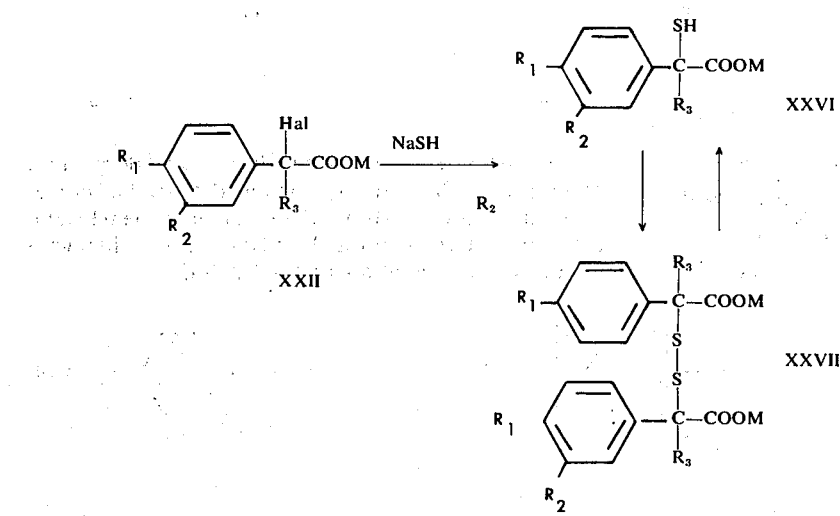

Reaction of a substituted α-halophenylacetic acid derivative of the Formulas XXI, II, XXII, or XXIII with thiourea at elevated temperatures, for instance, in boiling ethanol produces a 5-substituted-2-imino-4-oxothiazolidine of Formula XXVIII:

tional crystallization of their salts.

Reaction of a substituted α-halophenylacetic acid derivative of the Formulas XXI, XXIII, or II with thiourea at low temperatures produces a substituted α-isothioureidophenylacetic acid derivative of Formula XXX:

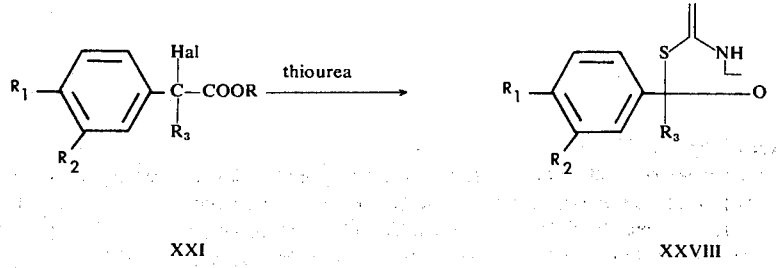

XXI     XXVIII

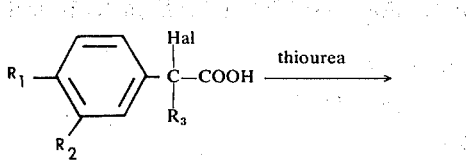 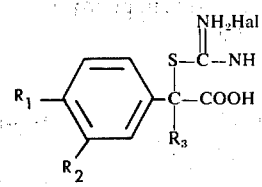

II

XXX

Reaction of a substituted α-halophenylacetic acid derivative of the Formulas XXI, XXIII, II, or XXII with an alkali lower alkylmercaptide produces a substituted α-lower alkylthiophenylacetic acid derivative of Formula XXXI in which R is a lower alkyl with 1 to 8 carbon atoms.

Reaction of a substituted α-halophenylacetic acid derivative of the Formulas XXI, II, XXIII, or XXII with an alkali thioalkanoate produces a substituted lower alkanoylthiophenylacetic acid of Formula XXXIII in which R is a lower alkyl with 1 to 8 carbon atoms:

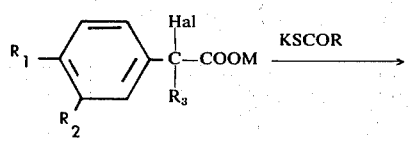 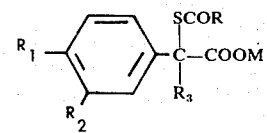

XXII

XXXIII

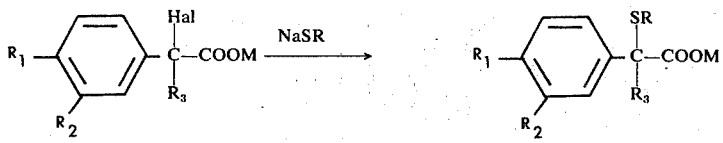

XXII

XXXI

Reaction of a substituted α-halophenylacetic acid derivative of the Formulas XXI, II, XXII, or XXIII with an alkali lower alkyl xanthate produces a substituted α-alkylxanthyl-phenylacetic acid derivative of the Formula XXXII in which R is lower alkyl of 1 to 8 carbons:

Reaction of a substituted α-halophenylacetic acid derivative of Formulas XXI, II, XXII, or XXIII with an alkali thiocyanate produces a substituted α-thiocyanophenylacetic acid derivative of Formula XXXIV:

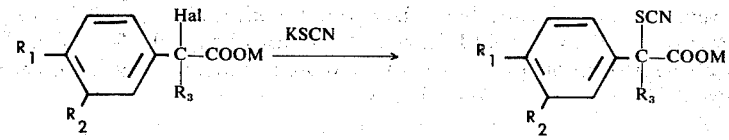

XXII

XXXIV

Reaction of a substituted α-halophenylacetic acid derivative of Formula XXI, II, XXII, or XXIII with an

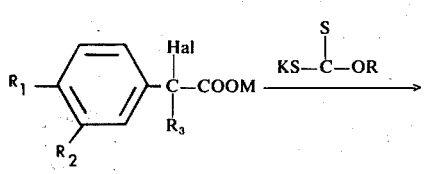 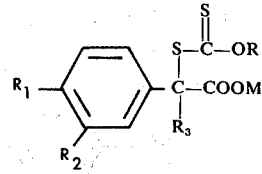

XXII

XXXII alkalicyanide produces a substituted α-cyanophenylacetic acid derivative of Formula XXXV:

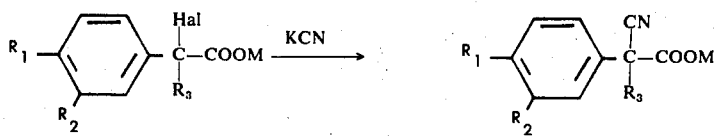

XXII

Reaction of a substituted α-halophenylacetic acid derivative of Formulas XXI, II, XXII, or XXIII with an alkali sulfide produces a substituted α,α'-thiodiacetic acid derivative of Formula XXXVI:

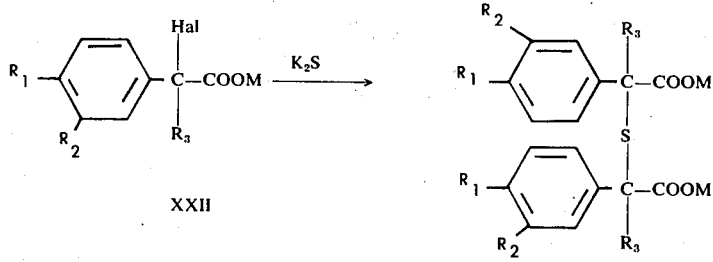

XXII

Reaction of a substituted α-halophenylacetic acid derivative of Formulas XXI, II, XXII, or XXIII with an alkali sulfite produces a substituted α-sulfophenylacetic acid derivative of Formula XXXVII:

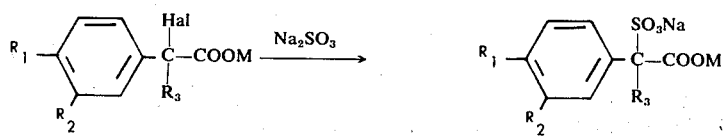

XXII   XXXVII

Reaction of a substituted α-phenylacetic acid derivative of Formulas XXI, II, XXII, or XXIII with an alkali thiosulfate produces a substituted α-thiosulfophenylacetic acid derivative of Formula XXXVIII:

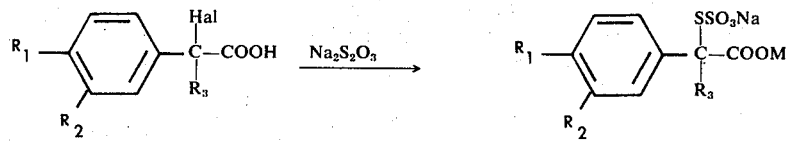

XXII   XXXVIII

Reaction of a substituted α-halophenylacetic acid derivative of Formulas XXI, II, XXII, or XXIII with an alkali alkanesulfinate produces a substituted α-alkylsulfonylphenylacetic acid derivative of Formula XXXIX, in which R is lower alkyl.

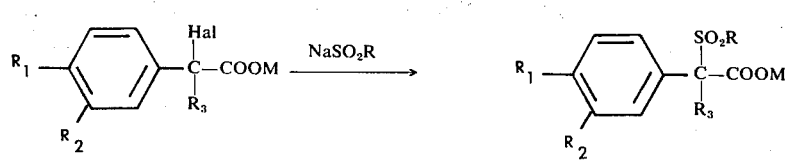

XXII   XXXIX

Substituted α-aminophenylacetic acids of Formula XLI in which R and R' are hydrogen or lower alkyl are prepared from substituted phenylglyoxylic acids of Formula XL with ammonia or a lower alkylamine and hydrogen over a Raney nickel or platinum catalyst. The substituted phenylglyoxylic acids of Formula XL are obtained from the corresponding substituted phenylglyoxylic acid lower alkyl esters of Formula VI by hydrolysis with aqueous-alcoholic alkali hydroxide or alkali carbonate.

catalyst. The oxime is obtained from the substituted phenylglyoxylic acid of Formula XL with hydroxylamine.

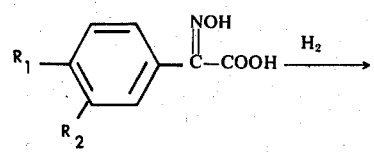

XLIII

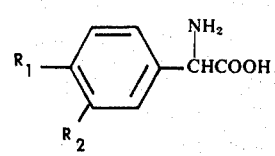

XLII

Dehydration of the substituted phenylglyoxylic acid oxime of Formula XLIII with boiling acetic anhydride leads to a substituted benzonitrile of Formula XLIV which, with a lower alkyl Grignard reagent, produces a substituted phenyl alkyl ketone of Formula XLV, in which $R_3$ is lower alkyl. The latter compound with ammonium chloride and sodium cyanide produces a

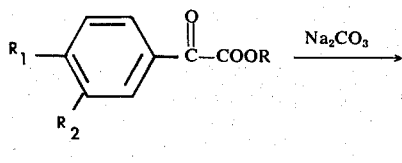

VI

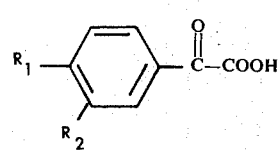

XI

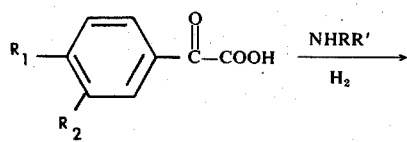

XL

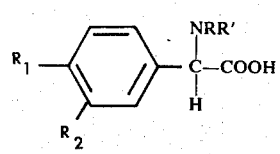

XLI

Substituted α-aminophenylacetic acids of Formula XLII, in which R and R' are hydrogen, may also be prepared by hydrogenation of a substituted phenylglyoxylic acid oxime of Formula XLIII over a platinum cyanohydrin of Formula XLVI which, upon acid hydrolysis, yields a substituted α-aminophenylacetic acid of Formula XL, in which $R_3$ is a lower alkyl.

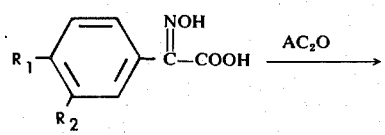

XLIII

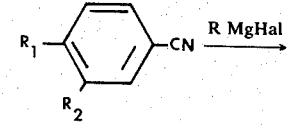

XLIV

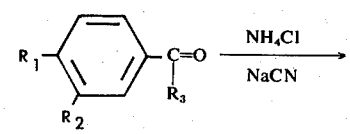

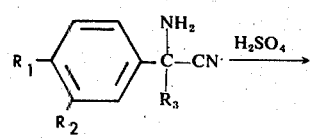

LXVI

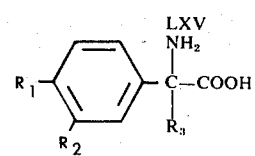

XL

The substituted phenylacetic acids of this invention and their carboxyl derivatives are racemic, and may be resolved into their optical isomers by standard procedures. Preferably a substituted phenylacetic acid is reacted in alcoholic or acetone solution with an equivalent amount of an optically active primary, secondary, or tertiary amine such as cinchonidine, cinchonine, quinine, ephedrine, α-methylbenzylamine, secondary butylamine, secondary amylamine, and others. The diastereomeric amine salts produced thereby, are separated by fractional crystallization, and each optically active salt is hydrolyzed with dilute mineral acid to produce the dextro or levo form, respectively, of the substituted phenylacetic acid. Alternatively, the lower alkyl ester of a substituted phenylacetic acid is reacted with an optically active primary or secondary amine such as ephedrine, α-methylbenzylamine, secondary butylamine, and others, to produce a mixture of diastereomeric substituted phenylacetamides which are separated by fractional crystallization. Each optically active phenylacetamide may be hydrolyzed with mineral acid to its respective optically active substituted phenylacetic acid.

Examples of compounds according to the present invention which, however, is not limited thereto, are:

1. α,m-Dichloro-p-cylcohexylphenylacetic acid
2. α,m-Dichloro-p-cyclohexylphenylacetic acid, sodium salt
2a. α,m-Dichloro-p-cycohexylphenylacetic acid, diethylammonium salt
3. 60 ,m-Dichloro-p-cycohexylphenylacetic acid, ethyl ester
4. α,m-Dichloro-p-cyclohexylphenylacetamide
5. α,m-Dichloro-p-cyclohexyl-N-isopropylphenylacetamide
6. α,m-Dichloro-p-cyclohexyl-α-methylphenylacetic acid
7. α-Bromo-m-chloro-p-cyclohexylphenylacetic acid
8. m-Bromo-α-chloro-p-cyclohexylphenylacetic acid
9. m-Chloro-p-cyclohexyl-α-mercaptophenylacetic acid
10. m-Chloro-p-cyclohexyl-α-acetomercaptophenylacetic acid
11. m-Chloro-p-cyclohexyl-α-methylmercaptophenylacetic acid
12. m-Chloro-p-cyclohexyl-α-methylsulfonylphenylacetic acid
13. m-Chloro-p-cyclohexyl-α-thiocyanophenylacetic acid
14. m-Chloro-p-cyclohexyl-α-aminophenylacetic acid
15. m-Chloro-p-cyclohexyl-α-acetaminophenylacetic acid
16. α,α-Di-(m-chloro-p-cyclohexylphenyl)-α,α'-dithiodiacetic acid
17. α-Chloro-p-cyclohexyl-m-nitrophenylacetic acid
18. α-Chloro-m-cyano-p-cyclohexylphenylacetic acid
19. α-Chloro-p-cyclohexyl-m-trifluoromethylphenylacetic acid
20. α,m-Dichloro-p-cyclopentylphenylacetic acid
21. α,m-Dichloro-p-cycloheptylphenylacetic acid
22. 5-(m-Chloro-p-cyclohexylpheny)-2,4-dioxothiazolidine
23. 5-(m-chloro-p-cyclohexylphenyl)-5-methyl-2-imino-4-oxothiazolidine
24. 2-(m-Chloro-p-cyclohexylphenyl)-2-imino-4-oxothiazolidine
25. α,α'-Di-(m-chloro-p-cyclohexylphenyl)-α,α'-thiodiacetic acid
26. α,o'-Dichloro-p-biphenylacetic acid
27. α,m-Dichloro-p-isobutylphenylacetic acid
28. m-Chloro-p-cyclohexyl-α-sulfophenylacetic acid, sodium salt
29. m-Chloro-p-cyclohexyl-α-thiosulfophenylacetic acid, sodium salt
30. m-chloro-p-cyclohexyl-α-cyanophenylacetic acid, sodium salt
31. m-Chloro-p-cyclohexyl-α-ethylxanthylphenylacetic acid, ethyl ester
3. o'-Bromo-α-chloro-p-biphenylacetic acid
33. α,m-Dichloro-p-sec.-amylphenylacetic acid
α-Chloro-o'-trifluoromethyl-p-biphenylacetic acid
35. α-Chloro-o'-nitro-p-biphenylacetic acid
36. α-Chloro-o'-cyano-p-biphenylacetic acid
37. m-Chloro-p-cyclohexyl-α-fluorophenylacetic acid
38. o'-Chloro-α-mercapto-p-biphenylacetic acid
39. m-Chloro-p-isobutyl-α-mercaptophenylacetic acid.
40. α,m-Dichloro-p-cyclohexylphenylacetic acid, benzyl ester.
41. α,m-Dichloro-p-cyclohexylphenylacetic acid, menthyl ester.
42. α,m-Dichloro-p-cyclohexylphenylacetic acid, cyclohexyl ester.
43. α,m-Dichloro-p-cyclohexylphenylacetic acid, phenyl ester.
44. α,m-Dichloro-p-cyclohexylphenylacetic acid, diethylaminoethyl ester.
45. α,m-Dichloro-p-cyclohexylphenylacetic acid, piperidinoethyl ester.

DESCRIPTION OF THE PREFERRED EMBODIMENTS

The following examples serve to illustrate the present invention without, however, limiting the same thereto.

EXAMPLE 1

α,m-Dichloro-p-cyclohexylphenylacetic acid ethyl ester

221.75 g. (0.747 mole) of the ethyl ester of m-chloro-p-cyclohexylphenylglycolic acid are stirred with 106.67 g. (0.895 mole) of thionylchloride at room temperature for 24 hours and then heated to reflux for 6 hours. The cold reaction mixture is poured into 1125 ml. of ice-cold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed by distillation under reduced pressure. Yield: 230.7 g. (97.9 %) of liquid, b.p. 118°–122° C./0.05 mm. Hg.

T.L.C.(silica): 5 $C_7H_8$; 4 HCOOET:1 HCOOH, $R_F$=0.86, 0.70 (trace).

Anal. Calculated for $C_{16}H_{20}Cl_2O_2$: 60.96 % C; 6.40 % H; 22.49 % Cl.

Found: 60.96 % C; 6.46 % H; 21.56 % Cl.

EXAMPLE 2

α,m-Dichloro-p-cyclohexylphenylacetic acid

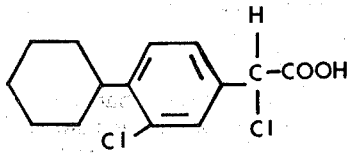

52.5 g. (0.167 moles) of the ethyl ester of α,m-dichloro-p-cyclohexylphenylacetic acid and 160 ml. of glacial acetic acid containing 40 ml. of 37% hydrochloric acid are refluxed for 20 hours. The mixture is concentrated under reduced pressure to give a gummy residue (47.1 g.). The latter material is dissolved in 300 ml of n-hexane, washed with ice-cold water (100 ml. total), dried over $Na_2SO_4$ (sodium sulfate), and filtered. The hexane is removed to give 47.2 g. of product.

TLC (silica): 5 $C_7H_8$: 4 HCOOEt : 1 HCOOH, $R_F$ = 0.64, 0.49 (trace).

EXAMPLE 3

α,m-Dichloro-p-cyclohexylphenylacetic acid sodium salt

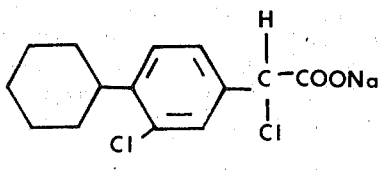

A solution of 12.4 g. of sodium bicarbonate in 135 ml. $H_2O$ is added dropwise to a stirred solution of 47.1 g. (0.164 moles) of α,m-dichloro-p-cyclohexylphenylacetic acid in 150 cc. of methanol. The solvent is removed in vacuum, and the residue is dried by repeated distillations with anhydrous ethanol. The crystalline residue is triturated with ether (100 cc.), collected on a filter, and washed with ether. After drying in a vacuum desiccator overnight, the crystalline product weighs 41.6 g. (91.3 %).

TLC(silica ): 5 $C_7H_8$:4 HCOOEt:1 HCOOH, $R_F$=0.62, 0.49 (trace)

Anal. Calculated for $C_{14}H_{15}Cl_2O_2Na$: 54.38 % C; 4.89 % H; 22.93 % Cl.

Found: 54.10 % C; 5.18 % H; 21.75 % Cl.

EXAMPLE 4

Diethylammonium salt of α,m-dichloro-p-cyclohexylphenylacetic acid

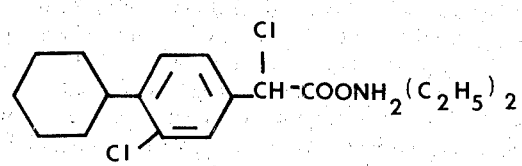

Anhydrous diethylamine (0.11 moles) is added dropwise to a stirred solution of α,m-dichloro-p-cyclohexylphenylacetic acid (0.10 moles) in 100 ml. of n-hexane at 0° C. The precipitated diethylammonium salt is collected on a filter, washed with n-hexane, and dried in a vacuum desiccator. Yield: 34 g., white crystals, M.P. 109°–115° C.

Anal. Calculated for $C_{18}H_{27}Cl_2NO_2$: 60.00 % C; 7.55 % H, 3.89 % N; 19.68 % Cl.

Found: 60.23 % C; 7.61 % H; 3.79 % N; 19.24 % Cl.

EXAMPLE 5

α,m-Dichloro-p-cyclohexyl-N-isopropylphenylacetamide

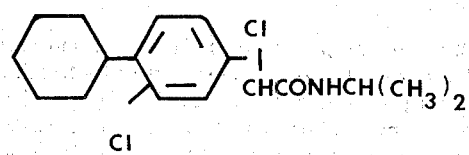

5 g. (0.016 moles) of the ethyl ester of α,m-dichloro-p-cyclohexylphenylacetic acid are stirred with 5.5 ml. of anhydrous isopropylamine and Linde 4A molecular sieve for 16 hours at room temperature. The reaction mixture is filtered and excess isopropylamine is removed in vacuum. The residue is taken up in ether and washed three times, each time with 15 ml. of 10% hydrochloric acid. The ether layer is dried over sodium sulfate, filtered, and the ether is removed. The residue is triturated with n-hexane to precipitate the amide, white crystals, M.P. 85°–87° C.

TLC (silica): 5 $C_7H_8$:4 HCOOEt; 1 HCOOH, $R_F$=0.75

Anal. Calculated for $C_{17}H_{23}Cl_2NO$: 62.20 % C; 7.06 % H; 4.27 % N; 21.60 % Cl.

Found: 61.49 % C; 6.98 % H; 4.21 % N; 20.64 % Cl.

EXAMPLE 6

α-Bromo-m-chloro-p-cyclohexylphenylacetic acid ethyl ester

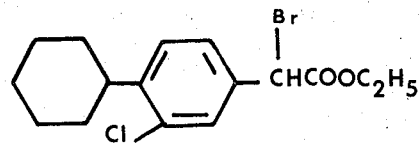

To 15.0 g. (0.0476 moles) of m-chloro-p-cyclohexylphenylglycolic acid ethyl ester there are added slowly with stirring at 40°–50° C. 23 g. (0.053 moles) of phosphorus pentabromide. The mixture is stirred at room tempeature for 16 hours, then diluted with 70 ml. of petroleum ether, and poured into 125 ml. of ice-cold water. The organic phase is separated, washed with saturated aqueous sodium hydrogen carbonate solution, dried over anhydrous sodium sulfate, filtered and the solvent removed in vacuo to leave 12.1 g. (70.8 %) of crude product. Distillation of the residue gives 8.1 g. (47.4 %) of a pale yellow liquid, b.p. 157°–161°C./0.10 mm. Hg.

TLC (silica): 5 $C_7H_8$: 4 HCOOEt:1 HCOOH, $R_F$=0.90
Anal. Calculated for $C_{16}H_{20}BrClO$:
Calculated: 53.42 % C; 5.60 % H; 32.08 % Cl + Br
Found: 53.42 % C; 5.42 % H; 31.6 % Cl + Br

EXAMPLE 7

Diethylammonium salt of α-bromo-m-chloro-p-cyclohexylphenylacetic acid

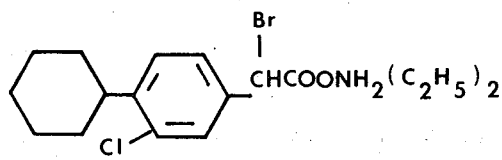

The salt is prepared from α-bromo-m-chloro-p-cyclohexylphenylacetic acid ethyl ester by treating the same with glacial acetic acid and 48 % hydrobromic acid, and conversion to the diethylammonium salt with diethylamine in an analogous manner as described in Examples 2 and 3.

EXAMPLE 8

Ethyl ester of α,m-dichloro-p-cyclohexyl-α-methylphenylacetic acid

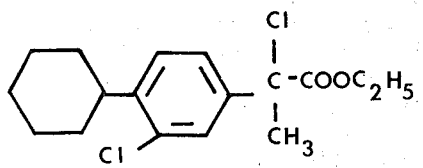

68.4 g. (0.330 moles) of phosphorus pentachloride are slowly added with stirring to 92.4 g. (0.300 moles) of m-chloro-p-cyclohexyl-α-methylphenylglycolic acid ethyl ester. The mixture is allowed to warm spontaneously and is stirred at room temperature for 16 hours. The cold reaction mixture is diluted with 340 ml. of petroleum ether and stirred with 500 ml. of ice water. The organic phase is separated and is then washed with cold 10 % sodium bicarbonate solution (twice with 90 ml. each time) followed by a water wash. The organic phase is dried over sodium sulfate, filtered, and the solvent is removed under reduced pressure to give 86.3 g. (87.5 %) of the above ester, b.p. 155°–158° C./0.35 mm. Hg.

TLC (silica): 5 $C_7H_8$:4 HCOOEt:1 HCOOH, $R_F$=0.90, 0.71 (trace)
Anal. Calculated for $C_{17}H_{22}Cl_2O_2$: 62.00 % C; 6.73 % H; 21.53 % Cl
Found: 62.92 % C; 6.43 % H; 21.62 % Cl.

EXAMPLE 9

Sodium salt of α-chloro-m-nitro-p-cyclohexylphenylacetic acid

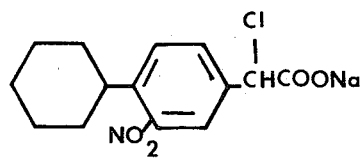

The salt is prepared in the same manner as described in Example 3 except that the starting material is m-nitro-p-cyclohexylphenylglycolic acid ethyl ester. The latter is obtained by nitration of p-cyclohexylphenylglyoxylic acid ethyl ester with fuming nitric acid at 0° C. and reduction with sodium borohydride.

EXAMPLE 10

Sodium salt of α-chloro-m-trifluoromethyl-p-cyclohexylphenylacetic acid

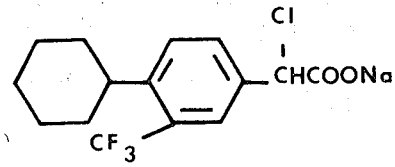

The salt is prepared in the same manner as described in Example 3 except that the starting material is p-cyclohexyl-m-trifluoromethylphenylglycolic acid ethyl ester. The latter is obtained from the corresponding m-bromo-p-cyclohexylglyoxylate ester with trifluoromethyl iodide and copper powder in dimethylformamide at about 150° C. followed by catalytic hydrogenation over platinum at 25° C. and 3 atm. pressure.

EXAMPLE 11

The sodium salt of α-chloro-m-cyano-p-cyclohexylphenylacetic acid

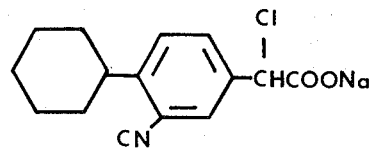

The salt is prepared in the same manner as described in Example 3 except that the starting material is m-cyano-p-cyclohexylphenylglycolic acid ethyl ester. The latter is obtained from the corresponding m-bromo-p-cyclohexylphenylglyoxylate ester with cuprous cyanide in quinoline at about 150° C., followed by catalytic hydrogenation over platinum at 25° C. and 3 atm. pressure.

EXAMPLE 12

Sodium salt of α,0'-dichloro-p-biphenylylacetic acid

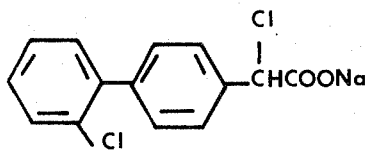

The salt is prepared in the same manner as described in Example 3 except that the starting material is o'-chloro-p-biphenylylglycolic acid ethyl ester.

EXAMPLE 13

Sodium salt of o'-bromo-α-chloro-p-biphenylylacetic acid

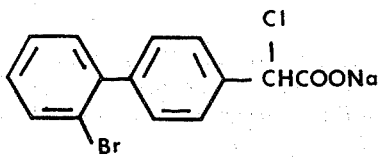

The salt is prepared in the same manner as described in Example 3 except that the starting material is 0'-bromo-p-biphenylylglycolic acid ethyl ester.

EXAMPLE 14

Sodium salt of α,m-dichloro-p-isobutylphenylacetic acid

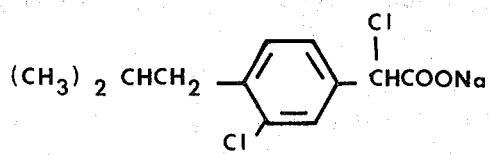

The salt is prepared in the same manner as described in Example 3 except that the starting material is m-chloro-p-isobutylphenylglycolic acid ethyl ester.

EXAMPLE 15

Sodium salt of α-chloro-0'-trifluoromethyl-p-biphenylylacetic acid

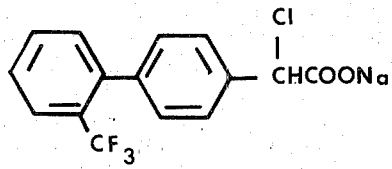

The salt is prepared in the same manner as described in Example 3 except that the starting material is o'-trifluoromethyl-p-biphenylylglycolic acid ethyl ester.

EXAMPLE 16

5-(m-Chloro-p-cyclohexylphenyl)-2-imino-4-oxo-thiazolidine

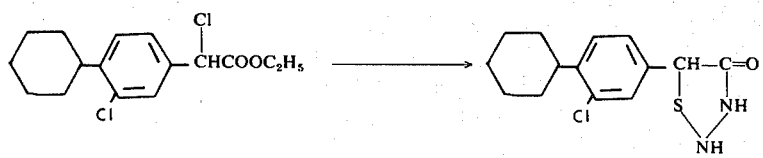

230.7 g. (0.732 moles) of the ethyl ester of α,m-dichloro-p-cyclohexylphenyl acetic acid are dissolved in 960 ml. of ethanol. To this solution there are added 66.9 g. (0.878 moles) of thiourea. The mixture is heated under reflux with stirring for 26 hours, whereupon the product precipitates out. The cold reaction mixture is diluted with 2.3 l. of water. The light yellow solid is collected on a filter and washed with 20% ethanol. The product is dried at 60° C. in a vacuum to remove most of the water, then stirred with 2 l. of anhydrous ether, collected by filtration, washed with anhydrous ether, and dried at 60: C. in a vacuum. Yield: 145.2 g. (64.3 %), m.p. 240°–242° C.
TLC (silica): 5 toluene: 4 HCOOEt: 1 HCOOH, $R_F=0.44$
Anal. Calculated for $C_{15}H_{17}ClNOS$: 58.34 % C; 5.55 % H; 9.07 % N; 11.48 % Cl; 10.38 % S
Found: 58.09 % C; 5.49 % H; 8.22 % N; 12.09 % Cl; 10.08 % S

EXAMPLE 17

5-[m-Chloro-p-cyclohexylphenyl]-2,4-dioxothiazolidine

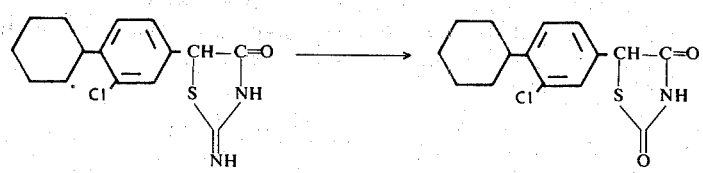

15.44 g. (0.05 moles) of 5-(m-chloro-p-cyclohexyl-phenyl)-2-imino-4-oxothiazolidine are refluxed with 200 ml. of 48% hydrobromic acid with stirring for 24 hours. The hydrobromic acid is removed by distillation under reduced pressure. The residue is extracted with ether. The etheral solution is washed with water and dried over anhydrous magnesium sulfate. After removing the drying agent and the solvent, the residue is triturated with n-hexane. The white solid which separates is collected by filtration, washed with n-hexane, and dried at 60° C. in a vacuum. Yield: 7.9 g. (51 %), M.P. 200.5° – 202.5° C.
TLC (silica): 5 $C_7H_8$: 4 HCOOEt: 1 HCOOH, $R_F$=0.67
Anal. Calculated for $C_{15}H_{16}ClNO_2S$: 58.15 % C; 5.21 % H; 4.52 % N; 11.44 % Cl; 10.35 % S
Found: 57.89 % C; 5.24 % H; 4.48 % N; 11.96 % Cl; 11.08 % S

EXAMPLE 18

α,α'-Di-[m-chloro-p-cyclohexylphenyl]-α,α'-dithiodiacetic acid

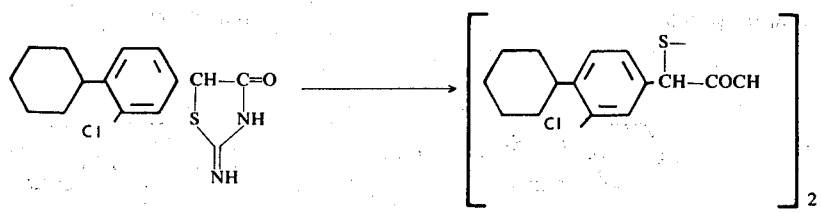

181.8 g. (0.427 moles) of 5-[m-chloro-p-cyclohexyl-phenyl]-2-imino-4-oxothiazolidine, 1 liter of 10% sodium hydroxide solution, and 325 ml. of 95% ethanol are refluxed with stirring for 20 hours. After distilling off the ethanol, the mixture is cooled to room temperature, washed three times wth ether, each time with 300 ml. of ether, and acidified with 310 ml. of 6N hydrochloric acid solution (1.86 moles) with stirring in the presence of 700 ml. of ether. The aqueous portion is extracted twice with ether, each time with 400 ml. of ether. The combined ethereal solution is dried over anhydrous magnesium sulfate and filtered. The solvent is removed under reduced pressure leaving the above acid.

EXAMPLE 19

Diethylammonium salt of α,α'di-[m-chloro-p-cyclohexylphenyl]-α',α'dithiodiacetic acid

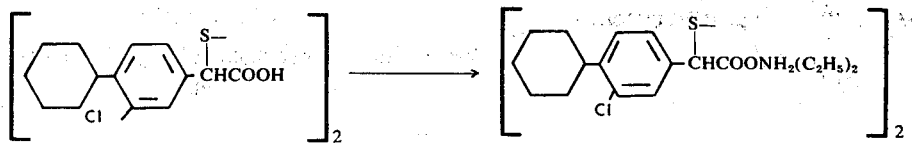

113 g. (0.199 moles) of crude α,α'-di-[m-chloro-p-cyclohexylphenyl]-α,α'-dithiodiacetic acid are dissolved in 800 ml. of anhydrous ether. To this solution there are added dropwise with stirring 33.2 g. (0.454 moles) of diethylamine diluted with 30 ml. of anhydrous ether. The mixture is stirred for 3 hours, whereupon the crude product precipitates out. The solid is collected on a filter and washed with anhydrous ether. The crude product is recrystallized from chloroform ethyl acetate; Yield: 37.8 g. (26.6 %) white solid, M.P. 137° – 130° C.
TLC (silica): 45 i-ProH : 30 ETOAc : 17 $Et_2NH$ : 8 $H_2O$, $R_F$=0.36
Anal. Calculated for $C_{36}H_{34}Cl_2N_2O_4S_2$: 60.57% C; 7.63% H; 9.93% Cl; 3.92% N; 8.98% S
Found: 59.83% C; 7.77 % H; 9.70% Cl; 3.90% N; 9.30% S

EXAMPLE 20

Diethylammonium salt of m-chloro-p-cyclohexyl-α-mercaptophenylacetic acid

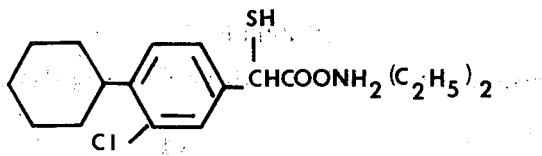

The chloroform-ethylacetate filtrate from Example 9 is evaporated to dryness in vacuo, and the residue is triturated with ether to precipitate the above salt, m.p. 103° – 109° C.
TLC: 25 EtOH: 3 $H_2O$: 4 $NH_4OH$ (28 %), $R_F$=0.81
m-Chloro-p-cyclohexyl-α-mercaptophenylacetic acid is also obtained by reducing α,α'-di-(m-chloro-p-cyclohexyl)-α,α'-dithioacetic acid with zinc amalgam and dilute sulfuric acid, or by reacting the sodium salt of α,m-dichloro-p-cyclohexylphenylacetic acid with excess aqueous-alcoholic sodium hydrosulfide under a nitrogenn atmosphere, and separating the mercaptan from the disulfide by fractional crystallization of the diethylammonium salts.

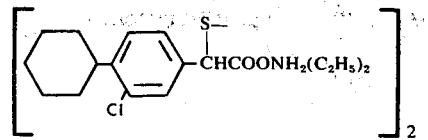

EXAMPLE 21

5-(m-Chloro-p-cyclohexylphenyl)-2-imino-5-methyl-4-oxothiazolidine

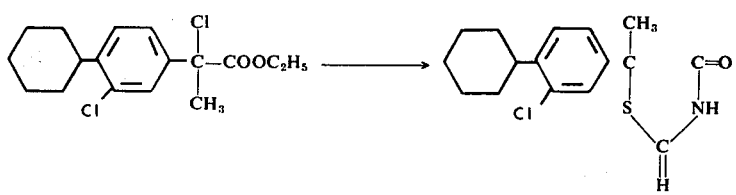

20.0 g. (0.0607 moles) of α,m-dichloro-p-cyclohexyl-α-methylphenylacetic acid ethyl ester and 5.3 g. (0.0699 moles) of thiourea are dissolved in 30 cc. of dry dimethylformamide and are heated in an oil bath at 105° C. for 24 hours. The dimethylformamide is removed under reduced pressure to leave a gum which upon trituration with water precipitates the crude product, which is collected on a filter, washed with water, and dried under vacuum. The crude product is dissolved in methanol, and diluted with ethyl acetate to give 4.4 g. (22.4 %) of purified product, m.p. 254°–259° C.

TLC (silica): 5 $C_7H_8$: 4 HCOOEt: 1 HCOOH, $R_F$=0.51

Anal. Calculated for $C_{16}H_{19}ClN_2OS$: 50.52% C; 5.93% H; 10.98% Cl; 9.93% S; 8.68% N Found: 59.34% C; 6.30% H; 10.98% Cl; 10.67% S; 8.44% N

EXAMPLE 22

Sodium salt of
m-chloro-p-cyclohexyl-α-acetothiophenyl acid

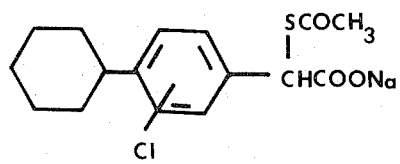

The sodium salt of α,m-dichloro-p-cyclohexylphenylacetic acid (0.050 moles) is reacted with purified sodium thioacetate (0.050 moles) in 100 ml. of anhydrous ethanol at 25°–80° C. under a nitrogen atmosphere for 4 to 8 hours. The precipitated sodium chloride is filtered off and the filtrate is concentrated to dryness in vacuo at 25° C. to leave the crude product as a residue. The latter is purified by recrystallization or by column chromatogrpahy.

EXAMPLE 23

Sodium salt of
m-chloro-p-cyclohexyl-α-methylthiophenylacetic acid

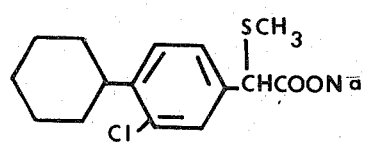

The procedure is the same as described in Example 22 except that sodium methylmercaptide is used in place of sodium thiolacetate.

EXAMPLE 24

Sodium salt of
m-chloro-p-cyclohexyl-α-methylsulfonylphenylacetic acid

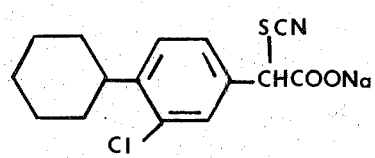

The procedure is the same as described in Example 22 except that sodium methanesulfinate is used in place of sodium thiolacetate.

EXAMPLE 25

Sodium salt of
m-chloro-p-cyclohexyl-α-thiocyanophenylacetic acid

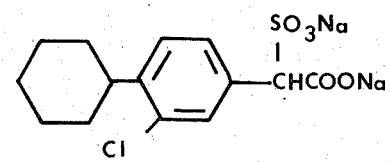

The procedure is the same as described in Example 22 except that sodium thiocyanate is used in place of sodium thiolacetate.

EXAMPLE 26

Sodium salt of
m-chloro-p-cyclohexyl-α-sulfophenylacetic acid

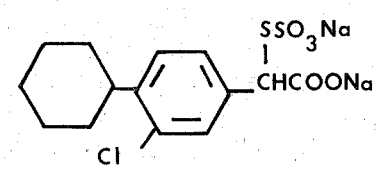

The procedure is the same as described in Example 22 except that sodium sulfite is used in place of sodium thiolacetate.

EXAMPLE 27

Sodium salt of
m-chloro-p-cyclohexyl-α-thiosulfophenylacetic acid

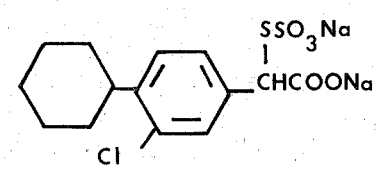

The procedure is the same as described in Example 22 except that sodium thiosulfate is used in place of sodium thiolacetate.

EXAMPLE 28

Sodium salt of m-chloro-p-cyclohexyl-α-ethylxanthylphenylacetic acid

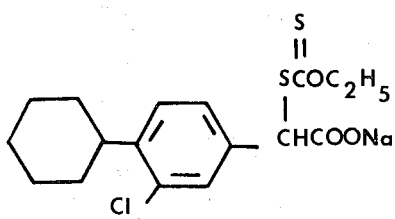

The procedure is the same as described in Example 22 except that sodium ethyl xanthate is used in place of sodium thiolacetate.

EXAMPLE 29

Sodium salt of m-chloro-p-cyclohexyl-α-cyanophenylacetic acid

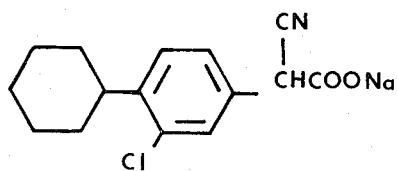

The procedure is the same as described in Example 22, except that sodium cyanide is used in place of sodium thiolacetate.

EXAMPLE 30

Sodium salt of α,α'-di-(m-chloro-p-cyclohexylphenyl)-α,α'-thiodiacetic acid

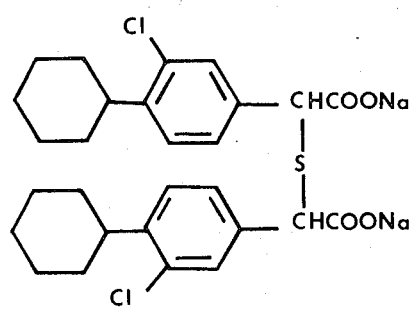

The procedure is the same as described in Example 22, except that sodium sulfide (0.025 moles) is used in place of sodium thiolacetate (0.050 moles).

EXAMPLE 31

Hydrochloride of m-chloro-p-cyclohexyl-α-isothioureidophenylacetic acid

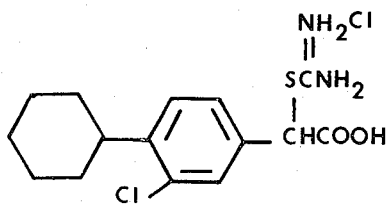

The procedure is the same as described in Example 22, except that thiourea is used in place of sodium thiolacetate, and the reaction is conducted at 0° C. with α,m-dichloro-p-cyclohexylphenylacetic acid (rather than with its sodium salt).

EXAMPLE 32 m-Chloro-p-cyclohexylphenylglyoxylic acid oxime

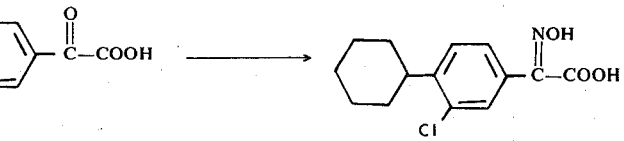

m-Chloro-p-cyclohexylphenylglyoxylic acid ethyl ester is hydrolyzed by heating with a 10% sodium carbonate solution for 24 hours. The cold reaction mixture is washed with ether, acidified with cold dilute hydrochloric acid, and extracted with ether. Removal of the ether leaves the carboxylic acid compound. 38.5 g. (0.144 moles) of m-chloro-p-cyclohexylphenylglyoxylic acid, 37.0 g. (0.45 moles) of sodium acetate, and 16 g. (0.23 moles) of hydroxylamine hydrochloride are stirred in 300 ml. of 50% aqueous ethanol at room temperature for 24 hours. The mixture is diluted with water, brought to a pH of 4.0 by the addition of hydrochloric acid, and extracted three times with ether. The combined ether extracts are dried over anhydrous magnesium sulfate, filtered, and concentrated under reduced pressure. On trituration with cyclohexane, 12 g. (29 1/2 %) of the oxime are obtained, M.P. 169.5° C. with decomposition. The oxime gives a red coloration with ferric chloride solution. On concentrating the filtrate and adding heptane, an additional amount of the oxime is obtained, 17.3 g. (42.5 %); total combined yield: 29.3 g. (72 %).

TLC (silica): $5C_7H_8$ : 4 HCOOEt: 1 HCOOH, $R_F$=0.46
Analysis: Calculated for $C_{14}H_{16}ClNO_3$: 59.68% C; 5.72% H; 12.59% Cl; 4.97% N
Found: 60.10% C; 5.80% H; 11.88% Cl; 4.89% N

EXAMPLE 33

α-Amino-m-chloro-p-cyclohexylphenylacetic acid

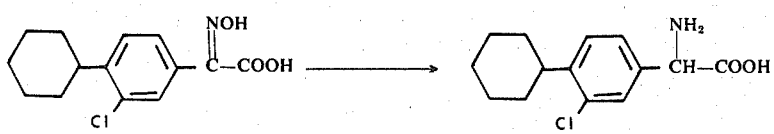

17.8 g. (0.0633 moles) of m-chloro-p-cyclohexylphenylglyoxylic acid oxime are dissolved in 90 ml. of methanol. Platinum oxide catalyst (0.5 g.) and 12 ml. of 6N hydrochloric acid (0.072 moles) are added, and the mixture is shaken with hydrogen at an initial pressure of 55 psi. Total uptake is 98 % of theory in 4 hours. The catalyst is filtered off and the solvent is distilled off under reduced pressure. The residue is triturated with water containing 5.9 g. (0.072 moles) of sodium acetate, filtered, and washed several times with water. The precipitate is stirred with anhydrous ether, filtered, and washed with ether.

Yield: 15 g. (89 %), M.P. 204°–205° C. with decomposition.

Analysis: Calculated for $C_{14}H_{18}ClNO_2 \cdot 1/2$ HCl: 58.79% C; 6.52% H; 18.60% Cl; 4.90%
Found: 59.52% C; 6.55% H; 18.67% Cl; 4.94% N

PHARMACEUTICAL COMPOSITIONS CONTAINING THE COMPOUNDS ACCORDING TO THE PRESENT INVENTION

The novel substituted phenylacetic acid compounds according to the present invention are preferably administered in therapy in the form of orally administrable solid shaped preparations such as tablets, dragees which may be enterically coated, pills, lozenges, or in powder or granule form, preferably enclosed in gelatin and the like capsules. Administration in liquid form, such as in the form of solutions, syrups, emulsions, suspensions, dispersions, fruit juices and the like is also possible.

Such powders, granules, and mixtures to be used in the preparations of tablets and other shaped and/or compressed preparations may be diluted by mixing and milling with a solid pulverulent extending agent to the desired degree of fineness or by impregnating the already milled, finely powdered, solid carrier with a suspension of said compounds in water or with a solution thereof in an organic solvent such as ethanol, methanol, acetone, and others and then removing the water or solvent.

When preparing tablets, pills, dragees, and the like shaped and/or compressed preparations, the commonly used diluting, binding, and disintegrating agents, lubricants, and other tableting adjuvants are employed, provided they are compatible with said substituted phenylacetic acid compounds. Such diluting agents and other excipients are, for instance, sugar, lactose, levulose, starch, bolus alba; as disintegrating and binding agents, gelatin, gum arabic, yeast extract, agar, tragacanth, methyl cellulose, pectin; and as lubricants stearic acid, talc, magnesium stearate, and others.

The compounds according to Formula I may also be administered parenterally, preferably in the form of their water soluble salt, for instance, in sterile isotonic aqueous solution.

Administration in the form of suppositories is, of course, also possible.

Such pharmaceutical compositions are prepared according to pharmaceutical compounding methods as they are conventionally used in the art.

The following examples of pharmaceutical compositions containing the active compounds of Formula I, their esters and/or their salts, serve to illustrate the preparation thereof without, however, being limited thereto.

EXAMPLE 34

25 g. of α,m-dichloro-p-cyclohexylphenylacetic acid ethyl ester and 175 g. of peanut oil are intimately mixed with each other. Portions of 200 mg. each of said mixture are filled into soft gelatin capsules. Each gelatin capsule thus contains 25 mg. of the active substituted phenylacetic acid ester of this invention.

EXAMPLE 35

100 g. of the diethylammonium salt of α,m-dichloro-p-cyclohexylphenylacetic acid, 1200 g. of starch (direct compression grade) as sold by the firm A. E. Staley Mfg. Co of Decatur, Ill. under the trademark STAREX, and 10 g. of magnesium stearate are thoroughly blended and compressed to give tablets, each containing 25 mg. of the active ingredient.

EXAMPLE 36

The mixture of Example 35 is compressed to biconcave dragee cores, each containing 25 mg. of the active ingredient. The cores are then provided in a manner known in the compounding art with an enteric shellac coating.

Of course, other dosage forms than capsules and tablets can be prepared by using well known compounding techniques and the α,m-dichloro-p-cyclohexylphenylacetic acid compounds used in Examples 34 to 36 can be replaced by other substituted phenylacetic acid compounds according to the present invention.

PHARMACOLOGICAL TESTS

A brief description of the pharmacological tests conducted with the compounds according to the present invention are given below:

Carrageenan Paw Edema

Of the substances used to induce local irritation, carrageenan was selected since most known nonsteroidal anti-inflammatory agents inhibit this inflammation.

Ten male rats per dose group (120–150 g.) were given one-half of the test material orally. Thirty minutes later, the remainder of the dose was given and 0.2 ml. of a 1% carrageenan solution was injected subdermally into the plantar surface of the hind paw. Each paw is marked as a consistent anatomical site, then immersed in a mercury bath to that point. The mercury bath is connected to a pressure transducer and the volume of displacement is read directly on a recorder. Three hours after drug administration, the hind paw volume is measured again. The increased volume is an index of edema. Treated groups are compared to a placebo-treated group to calculate the percent inhibition of edema.

Filter Paper Granuloma

This assay was used to evaluate anti-inflammatory agents and to determine the lowest dose which produces significant inhibition of granuloma growth. This assay has the advantage of being semi-acute (4 to 7 days). The usual end point involves obtaining the wet weight as well as the dry weight of the granuloma.

Small discs of filter paper saturated with carrageenan were placed subcutaneously in each rat on the first day of the study. Test compound was administered orally on a b.i.d. basis on Day 1 to Day 4. On Day 5, a single dose was given in the morning and the animals were sacrificed in the afternoon. Both filter paper discs were removed and trimmed of extraneous tissue and then weighed. After drying in an oven over the weekend, the dry weight was obtained. Activity was determined by the difference in granuloma weight between a placebo-treated control group and the drug-treated groups.

Randall-Selitto Analgesia Test

In accordance with the Randall-Selitto test for measuring the pain threshold, the pressure needed on a metal plunger to give a "pain reponse" in a rat when the plunger is placed in the yeast-inflamed hind paw of a rat is measured. Following measurement of control pain threshold, yeast was injected into the paw and the test compound was given orally. The pain threshold was measured at hourly intervals and compared to a placebo-treated control group.

Anti-Pyretic Assay

Brewer's yeast was injected subcutaneously in rats and rectal temperatures were obtained at the end of five hours. Those rats (10 per group) having a significant fever were given test compounds and rectal temperatures were measured at hourly intervals for 2 to 3 hours. (A positive response occurs when rectal temperature decreases by 1° C. or more).

Phenylquinone analgesia

Mice were pre-treated orally with test compound and then given 1.25 mg./kg. of phenylquinone i.p to produce a series of "writhes" (severe intestinal contractions). The number of writhes was recorded. The percent decrease was calculated from the incidence of writhes in a placebo-treated control group.

Ultra-violet Erythema in Guinea Pigs

Erythema associated with inflammation was used in the assay. Restricted areas of a guinea pig were exposed to a controlled ultra-violet light and after two hours the exposed areas were graded for the extent of erythema.

Polyarthritis in rats

Twelve rats per dose group were treated (b.i.d.) starting the day before injection of adjuvant. Paw volumes were measured for both hind paws on several days during and following drug treatment. Drug was given for a period of 15 days. The paw volume was compared to an untreated control group to determine volume increase. Drug action was calculated as the percent decrease in paw volume (inflammation) as compared to an adjuvant-treated control. Gross signs of inflammation were scored on a weekly basis and drug action calculated as a decrese in total score. Body weights were recorded at intervals.

Acute Toxicity

Groups of ten (10) male mice (18g. to 24 g.) were treated with various doses of drug and were observed for nine days following drug administration. Food and water were delivered ad lib. The drug to be tested was prepared as a water suspension using one drop of "Tween 80" per 10 ml. and administered orally as a single dose (10 ml./kg.). The control group received the vehicle only (10 ml./kg.). The lethal dose ($LD_{50}$) which is the dose of drug required to kill 50 percent of the animals tested, was determined by the Litchfield and Wilcoxon method.

The following compounds were tested:

Sodium salt of $\alpha$,m-dichloro-p-cyclohexylphenylacetic acid, designated as 539A;

Diethylammonium salt of m-chloro-p-cyclohexyl-$\alpha$-mercaptophenylacetic acid, designated as 528A;

Diethylammonium salt of $\alpha,\alpha'$-di-(m-chloro-p-cyclohexylphenyl)-$\alpha',\alpha'$-dithiodiacetic acid, designated as 531A;

5-(m-Chloro-p-cyclohexylphenyl)-2-imino-4-oxo-thiazolidine, designated as 530;

5-(m-Chloro-p-cyclohexylphenyl)-2,4-dioxothiazolidine, designated as 529;

$\alpha$,m-Dichloro-p-cyclohexylphenylacetic acid ethyl ester, designated as 541.

The test results are given in the following Table wherein the following legends were employed:

| | |
|---|---|
| PQW | phenylquinone writhing |
| RSA | Randall-Selitto Analgesia |
| CPE | Carrageenan Paw Edema |
| UVS | Ultra-Violet Erythema |
| FPG | Filter Paper Granuloma |
| AP | Anti-Pyresis |
| P.T. | Pain Threshold |
| No. P/T | Number Positive/Total |
| % | Percentage Increase |
| % | Percentage Inhibition |

POLYARTHRITIS

| COMPOUND | DOSE mg/kg | ROUTE | PQW % | ED$_{50}$ | CPE % | RSA % PT | AP No. P/T | UVE No. P/T | UVE ED$_{50}$ | injected hind-paw | noninjected hind-paw | secondary lesions | EPG % wet | EPG % dry | ACUTE TOXICITY LD$_{50}$ |
|---|---|---|---|---|---|---|---|---|---|---|---|---|---|---|---|
|  | 1 | P.O |  |  |  | 10 |  |  |  |  |  |  |  |  |  |
|  | 2 | P.O | 13.1 |  |  | 30.3 |  |  |  |  |  |  |  |  |  |
|  | 3.125 | P.O |  | 34.6 |  | 29.5 |  |  |  |  |  |  |  |  |  |
|  | 5 | P.O | 13.1 |  |  | 29.5 |  |  |  |  |  |  |  |  |  |
|  | 6.25 | P.O |  | 9.6 | 42.0 |  | 0/8 |  |  |  |  |  |  |  |  |
| 539A | 10 | P.O | 54.6 |  |  |  |  |  |  | 41.8 | 14.1 | 28.2 |  |  | 430mg/kg |
| 12.5 | P.O |  | 47.2 |  |  | 3/8 |  |  |  |  |  |  |  |  |  |
|  | 20 | P.O | 84.5 |  |  |  |  |  |  |  |  |  |  |  |  |
|  | 25 | P.O |  |  | 43.0 | 41.8 | 2/8 |  |  | 50.2 | 12.1 | 44.0 | 31.7 | 41.1 |  |
|  | 30 | P.O. | 96.6 |  |  |  |  |  |  |  |  |  |  |  |  |
|  | 50 | P.O |  |  | 52.0 | 49.3 | 6/8 |  |  | 45– | 59.6– | 39.3– | 43.9 | 38.8 |  |
|  | 100 | P.O |  |  | 64.0 | 77.6 | 8/8 |  |  | 59.1 | 51.2 | 30.1 |  |  |  |
|  | 5 | P.O |  |  |  |  |  | 5/8 |  |  |  |  |  |  |  |
|  | 10 | P.O |  |  |  |  |  | 5/8 | 10.5 |  |  |  |  |  |  |
| 528A | 25 | P.O |  |  |  |  |  | 7/8 |  |  |  |  |  |  |  |
|  | 50 | P.O |  |  |  |  |  |  |  |  |  |  |  |  |  |
|  | 100 | P.O |  |  | 52.0 |  |  |  |  | 52.8 | 35.6 | 34.0 |  |  |  |
|  | 50 | P.O |  |  |  | 32 | 1/8 |  |  |  |  |  |  |  |  |
| 531A | 100 | P.O |  | 19.9 | 28 |  | 1/8 |  |  | 34.0– | 44.7– | 30.3– |  | >2000 |  |
|  | 200 | P.O |  |  |  | 51 | 6/8 |  |  | 35.6 | 43.8 | 43.6 |  |  | mg/kg |
|  | 50 | P.O |  |  |  |  |  |  |  |  |  |  |  |  |  |
| 530 | 100 | P.O |  |  | 51.4 |  |  |  |  | 38.1 | 44.7 | 17.3 |  |  |  |
|  | 200 | P.O |  |  |  |  |  |  |  |  |  |  |  |  |  |
|  | 50 | P.O |  |  | 17.4 |  |  |  |  |  |  |  |  |  |  |
| 529 | 100 | P.O |  |  | 30 |  | 1/8 |  |  | 42.0 | 17.3 | 21.0 |  |  |  |
|  | 200 | P.O |  |  |  |  |  |  |  |  |  |  |  |  |  |
|  | 6.25 | P.O |  |  | 51.3 |  |  |  |  |  |  |  |  |  |  |
| 541 | 12.5 | P.O |  |  | 38.8 |  |  |  |  |  |  |  |  |  |  |
|  | 25. | P.O |  |  | 49.8 |  |  |  |  |  |  |  |  |  |  |
|  | 50 | P.O |  |  | 52.2 |  |  |  |  |  |  |  |  |  |  |

CLINICAL UTILITY

The compounds of Formula I, their esters, and their salts have proved to be potent anti-inflammatory drugs with a high analgesic and antipyretic activity. They are administered to patients suffering from rheumatoid arthritis, rheumatoid spondylitis, osteoarthritis, acute gouty arthritis, bursitis, and other arthritic disorders. The esters of said compounds and especially the ethyl ester of α,m-dichlorocyclohexylphenylacetic acid have proved to be especially useful as they are better tolerated and not as irritating on the gastrointestinal tract as the free acids.

As stated hereinabove, the compounds of Formula I, their esters, and their salts are preferably administered in a dose of 0.1 mg./kg. to 10 mg./kg. given once to four times daily. Thus the actual dose may vary between about 5 mg. and about 500 mg. once to four times daily which dose is preferably administered orally.

As stated hereinabove, the starting materials, i.e. the lower alkyl esters of substituted phenylglycolic acids as well as of substituted phenylglyoxylic acids are prepared according to processes described in copending application Ser. No. 767,058 now U.S. Pat. No. 3,704,313 of one of the Applicants of the present application, which application was filed Oct. 10, 1968 under the title "p-CYCLOALKYLPHENYLGLYCOLIC ACID AND DERIVATIVES THEREOF". Said application Ser. No. 767,058 now U.S. Pat. No. 3,704,313 and its contents thus are incorporated by reference into the present application.

We claim:

1. A compound of the formula

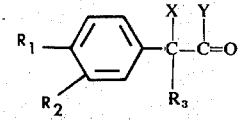

where $R_1$ is a member selected from the group consisting of cycloalkyl with 5 to 7 carbon atoms, lower alkyl substituted cycloalkyl, alkyl with 1 to 8 carbon atoms, phenyl, and phenyl substituted by a member selected from the group consisting of trifluoromethyl, halogen, lower alkylsulfonyl, and nitro;

$R_2$ is a member selected from the group consisting of halogen, nitro, trifluoromethyl and lower alkylsulfonyl, and if $R_1$ is substituted phenyl, hydrogen;

$R_3$ is a member selected from the group consisting of hydrogen and lower alkyl with 1 to 8 carbon atoms;

X is amino, lower alkanoylamino, di-(lower alkyl)amino; or lower alkylamino; and Y is hydroxyl.

2. The compound of claim 1, said compound being dextrorotary.

3. The compound of claim 1, said compound being levorotary.

4. α-amino-m-chloro-p-cyclohexylphenylacetic acid

5. α-acetamino-m-chloro-p-cyclohexylphenylacetic acid

6. The compound of claim 1 where:

$R_1$ is cycloalkyl;

$R_2$ is halogen;

X is amino, lower alkanoylamino, di(loweralkyl)amino or loweralkylamino; and

Y is hydroxyl.

* * * * *